US011372905B2

(12) United States Patent
Chakrapani et al.

(10) Patent No.: US 11,372,905 B2
(45) Date of Patent: Jun. 28, 2022

(54) ENCODING-ASSISTED ANNOTATION OF NARRATIVE TEXT

(71) Applicant: International Business Machines Corporation, Armonk, NY (US)

(72) Inventors: Nakul Chakrapani, Santa Clara, CA (US); Ramani Routray, San Jose, CA (US); Pathirage Perera, San Jose, CA (US); Sheng Hua Bao, San Jose, CA (US); Orna Raz, Haifa (IL); Eitan Farchi, Pardes Hana (IL)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 72 days.

(21) Appl. No.: 16/266,610

(22) Filed: Feb. 4, 2019

(65) Prior Publication Data
US 2020/0250209 A1    Aug. 6, 2020

(51) Int. Cl.
*G06F 16/31*    (2019.01)
*G16H 15/00*    (2018.01)
(Continued)

(52) U.S. Cl.
CPC .......... *G06F 16/313* (2019.01); *G06F 40/169* (2020.01); *G06F 40/20* (2020.01); *G16H 15/00* (2018.01)

(58) Field of Classification Search
CPC ...... G06F 16/313; G06F 40/169; G06F 40/20; G16H 15/00
See application file for complete search history.

(56) References Cited

U.S. PATENT DOCUMENTS 7,461,006 B2    12/2008 Gogolak
2007/0143298 A1*    6/2007 Surendran ............ G06Q 10/107
(Continued)

FOREIGN PATENT DOCUMENTS

WO    2018057359 A1    3/2018

OTHER PUBLICATIONS

Sunghwan Sohn, Cheryl Clark, Scott R Halgrim, Sean P Murphy, Christopher G Chute, Hongfang Liu, "MedXN: an open source medication extraction and normalization tool for clinical text", Journal of the American Medical Informatics Association, vol. 21, Issue 5, Sep. 2014, pp. 858-865 (Year: 2014).*
(Continued)

*Primary Examiner* — Hope C Sheffield
(74) *Attorney, Agent, or Firm* — Garg Law Firm, PLLC; Rakesh Garg; John Noh (57) ABSTRACT

From metadata corresponding to a narrative text, a first encoding is constructed, the first encoding comprising a standardized text string, the first encoding formed according to an encoding scheme. A specified portion of the standardized text string of the first encoding is marked as an anchor term. A correspondence between the first encoding and a second encoding is tested using the encoding scheme and a Natural Language Processing engine, responsive to finding the anchor term within the narrative text. The second encoding corresponds to a text window. The text window comprises a portion of the narrative text comprising an instance of the anchor term and a word within a predetermined distance from the instance. Responsive to the second encoding being identical to the first encoding, the narrative text is annotated, the annotating creating new data linking the narrative text with the second encoding.

14 Claims, 7 Drawing Sheets

(51) Int. Cl.
*G06F 40/20* (2020.01)
*G06F 40/169* (2020.01)

(56) References Cited

U.S. PATENT DOCUMENTS

| | | | |
|---|---|---|---|
| 2009/0119095 A1* | 5/2009 | Beggelman | G06F 40/30 |
| | | | 704/9 |
| 2014/0006013 A1 | 1/2014 | Markatou et al. | |
| 2014/0181128 A1* | 6/2014 | Riskin | G06F 16/3344 |
| | | | 707/756 |
| 2016/0048655 A1 | 2/2016 | Maitra et al. | |
| 2017/0091164 A1* | 3/2017 | Bao | G06F 40/284 |
| 2019/0130073 A1* | 5/2019 | Sun | G06K 9/6223 |

OTHER PUBLICATIONS

M. Viell, Head Medical Coding, Bayer AG, "IBM Watson for Medical Coding," Apr. 2018, https://www.meddra.org/sites/default/files/page/documents_insert/ibm_watson_april_2018_0.pdf.
S. Comfort, "Sorting Through the Safety Data Haystack: Using Machine Learning to Identify Individual Case Safety Reports in Social-Digital Media," Drug Safety 41.6 (2018): 579-590.
A. Winter, "How can Natural Language Processing help MedDRA coding?" Apr. 16, 2018, https://www.meddra.org/sites/default/files/page/documents_insert/linguamatics_nlp_meddra_coding_13apr.pdf.
K. Lee, "Adverse Drug Event Detection in Tweets with Semi-Supervised Convolutional Neural Networks." In Proceedings of the 26th International Conference on World Wide Web (WWW '17), Apr. 3-7, 2017, Perth, Australia.
M. Dupuch, "Automatic creation and refinement of the clusters of pharmacovigilance terms." Proceeding IHI '12 Proceedings of the 2nd ACM SIGHIT International Health Informatics Symposium, pp. 181-190, Miami, Florida, USA—Jan. 28-30, 2012.

* cited by examiner

ENCODING-ASSISTED ANNOTATION OF NARRATIVE TEXT

TECHNICAL FIELD

The present invention relates generally to a method, system, and computer program product for classifying narrative text. More particularly, the present invention relates to a method, system, and computer program product for encoding-assisted annotation of narrative text.

BACKGROUND

Natural language processing (NLP) is a field of computer science, artificial intelligence, and linguistics concerned with the interactions between computers and human (natural) languages. As such, NLP is often a component of natural language understanding, i.e. enabling computers to derive meaning from human or natural language input, and natural language generation. NLP mechanisms generally perform one or more types of lexical or dependency parsing analysis including morphological analysis, syntactical analysis or parsing, semantic analysis, pragmatic analysis, or other types of analysis directed to understanding textual content. Modern NLP algorithms use machine learning, especially statistical machine learning to automatically learn rules for interpreting textual content through analyzing large corpora of typical real-world examples. A corpus (plural, "corpora") is a set of documents (or sometimes, individual sentences) that have been hand-annotated with the correct values to be learned.

One common NLP task is to represent a narrative text description with an encoding according to a standardized terminology or encoding scheme, such as a combination of letters and numbers or a short, standardized text string. A standardized encoding scheme, as used herein, represents narrative text with a standard encoding from a fixed, predetermined list of standard encodings. Each standard encoding is a standardized text string itself or corresponds to a specific, standardized text string. Narrative text is variable, and there is often more than one way to convey the same information; representing such narrative text with a standard encoding alleviates this problem. For example, the narrative text descriptions "Patient reported that her head hurts," "Patient reported head pain," and "Patient reports she thinks she has a migraine headache," all refer to a headache. Thus, all three descriptions can be represented with one standard encoding, for "headache". The most important reason to represent narrative text data into a standardized terminology is to more easily analyze such data.

One non-limiting example standardized encoding scheme is the Medical Dictionary for Regulatory Activities (MedDRA) Terminology. (MedDRA is a registered trademark of the International Federation of Pharmaceutical Manufacturers and Associations (IFPMA) in the United States and other countries). MedDRA is an international medical terminology dictionary used in, for example, the pharmaceutical industry. MedDRA is a five-level hierarchy. At the lowest, most specific level, "Lowest Level Terms" (LLTs) reflect how an observation might be reported in practice. Each member of the next higher level, "Preferred Terms" (PTs), is a distinct descriptor—for example, for a symptom or diagnosis. Related PTs are grouped together into "High Level Terms" (HLTs). HLTs are in turn grouped into "High Level Group Terms" (HLGTs). Finally, at the highest level, HLGTs are grouped into "System Organ Classes" (SOCs). For example, MedDRA LLTs and PTs are commonly used when tracking medical events, such as adverse reactions to medications, for reporting to regulatory authorities. This non-limiting example arrangement of encodings is a tree-like hierarchy in which the encodings are arranged according to the granularity of the concept represented by the encoding. the standardized encoding can be a flat list, a hierarchical arrangement of encoding by categories, an ontology of a suitable structure, or other arrangements as might be useful in a given implementation.

Another example standardized encoding scheme is International Classification of Diseases, Tenth Revision, Clinical Modification (ICD-10-CM), used in the United States to encode diagnoses and other medical information. ICD-10-CM is a seven-character, alphanumeric encoding. Each encoding begins with a letter, and that letter is followed by two numbers. The first three characters of ICD-10-CM are the "category", describing the general type of the injury or disease. The category is followed by a decimal point, the subcategory, and up to two sub-classifications, which further explain the cause, manifestation, location, severity, and type of injury or disease. The last character is the extension, describing what type of encounter with a healthcare provider is involved (e.g. initial or subsequent). Thus, although ICD-10-CM is an alphanumeric encoding, each encoding corresponds to a standardized text string.

Other example standardized encoding schemes include the World Health Organization (WHO) Drug Dictionary, for identifying and tracking drug names, and the Diagnostic and Statistical Manual of Mental Disorders (DSM), a common language and standard criteria for the classification of mental disorders.

SUMMARY

The illustrative embodiments provide a method, system, and computer program product. An embodiment includes a method that constructs, from metadata corresponding to a narrative text, a first encoding, the first encoding comprising a standardized text string, the first encoding formed according to an encoding scheme. An embodiment marks, as an anchor term, a specified portion of the standardized text string of the first encoding. An embodiment tests a correspondence between the first encoding and a second encoding, using the encoding scheme and a Natural Language Processing engine, responsive to finding the anchor term within the narrative text, the second encoding corresponding to a text window, the text window comprising a portion of the narrative text comprising an instance of the anchor term and a word within a predetermined distance from the instance. An embodiment annotates, responsive to the second encoding being identical to the first encoding, the narrative text, the annotating creating new data linking the narrative text with the second encoding.

An embodiment includes a computer usable program product. The computer usable program product includes one or more computer-readable storage devices, and program instructions stored on at least one of the one or more storage devices.

An embodiment includes a computer system. The computer system includes one or more processors, one or more computer-readable memories, and one or more computer-readable storage devices, and program instructions stored on at least one of the one or more storage devices for execution by at least one of the one or more processors via at least one of the one or more memories.

BRIEF DESCRIPTION OF THE DRAWINGS

Certain novel features believed characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

DETAILED DESCRIPTION

Traditionally, manual efforts have been required to reduce narrative text descriptions to corresponding encodings according to an encoding scheme. However, such work is tedious, time-consuming, and often results in inconsistent coding. For example, one coder might encode the narrative description, "Patient reported head pain," as "headache" while another might encode the same description as "pain". As a result, those who must process and maintain databases of such descriptions and associated data are interested in automating the encoding process using supervised learning approaches such as a neural network-based supervised learning approach.

Implementing a supervised learning approach requires training data with which to implement supervised learning. Traditionally, training data has been generated by human analysts evaluating and annotating a narrative text description. As used herein, annotating refers to assigning a standardized encoding to a portion of narrative text. Thus, annotating results in an association between a portion of narrative text and an encoding, within a standardized encoding scheme, representing the text. The annotated text is then usable as training data—for example, for a neural network intended to assign encodings, within the same encoding scheme, to new narrative text. For example, if a neural network has been trained that the narrative descriptions "Patient reported that her head hurts," "Patient reported head pain," and "Patient reports she thinks she has a migraine headache," all correspond to the standardized encoding "headache", when the neural network evaluates a new narrative text description as similar (within the neural network's predefined threshold of similarity) to the training data, the neural network also classifies the new narrative text description as "headache" as well. Other supervised learning approaches, using other implementations besides a neural network-based implementation, can also be conducted using training data in a similar manner.

The illustrative embodiments recognize that having humans perform annotations is time consuming and error prone. Many annotations require fine distinctions between similar encodings. Individual humans vary in their coding of such fine distinctions, and one individual will likely not apply encodings completely consistently with another's encodings. Human annotators may also mis-code semantic variations of a particular event. For example, a human annotator may annotate "trouble in stomach" and "stomach pain" differently, even though both should be annotated with the same encoding.

The illustrative embodiments also recognize that much of the necessary data used in annotation already exists, but is not sufficiently linked to the text being described. In many cases, narrative text descriptions have already been encoded, by human subject matter experts, and saved, for example in document metadata. For example, pharmaceutical manufacturers regulated by the United States Food and Drug Administration are required to maintain records of adverse medical events related to medications. An adverse event is any untoward medical occurrence in a patient or clinical investigation subject administered a pharmaceutical product; the adverse event does not necessarily have a causal relationship with the treatment. Such adverse event reports are collected in narrative text form, encoded appropriately, and the coding used for tracking and reporting purposes. However, such coding refers to an entire report, and does not associate a specific portion of narrative text with a specific encoding. Further, a report may include more than one event, and be associated with more than one encoding, without a clear distinction as to which encoding refers to which portion of text. However, such encoding remains useful data, already assigned and validated by human subject matter experts, and can be leveraged to create the necessary training data.

Consequently, the illustrative embodiments recognize that there is a need to associate a specific portion of narrative text with a specific related encoding, for use in generating training data for a supervised learning approach, such as a neural network intended to understand and apply the encoding scheme to new narrative text.

The illustrative embodiments recognize that the presently available tools or solutions do not address these needs or provide adequate solutions for these needs. The illustrative embodiments used to describe the invention generally address and solve the above-described problems and other problems related to encoding-assisted annotation of narrative text.

An embodiment can be implemented as a software application. The application implementing an embodiment can be configured as a modification of an existing NLP system, as a separate application that operates in conjunction with an existing NLP system, a standalone application, or some combination thereof.

Particularly, some illustrative embodiments provide a method by which metadata corresponding to a narrative text can be used to annotate a specific portion of the narrative text.

An embodiment receives, for annotation, a narrative text description and metadata corresponding to the narrative text description. The metadata includes at least one encoding, formed according to a standardized encoding scheme, corresponding to the narrative text. The embodiment's goal is to apply an annotation linking the encoding to a portion of the narrative text.

Examples from medical narrative encoding based on MedDRA and other example encoding schemes are used only for the clarity of the description and not to imply any limitation on the illustrative embodiments. From this disclosure, those of ordinary skill in the art will be able to adapt an embodiment to many other standard as well as proprietary encoding schemes to encode narrative content from a variety of subject-matter domains, and such adaptations are contemplated within the scope of the illustrative embodiments.

For example, the narrative text description might be an example of an adverse event related to a medication, and metadata corresponding to the narrative text description might include one or more encodings according to the MedDRA standardized encoding scheme. In particular, such a narrative text description might be, "Patient experienced headache and trouble in stomach after taking Medication A." Two MedDRA Preferred Terms corresponding to this narrative text description might be "headache" and "stomach pain". However, the MedDRA Preferred Terms refer to the narrative text description as a whole, rather than a specific portion of the narrative text description. To create training data, an annotation must be created that links a specific encoding to a specific portion of the narrative text.

As another example, the narrative text description might be an example of a report of a patient encounter with a medical provider, and metadata corresponding to the narrative text description might include one or more encodings according to the ICH-10-CM standardized encoding scheme. In particular, a portion of such a narrative text description might be, "Patient presents with bruising and a swollen right index finger after contact in a rugby match. Patient has not lost consciousness. Examination shows no rupture of the skin on the right hand. X-rays confirm a closed fracture of distal phalanx of right index finger." An ICH-10-CM diagnostic encoding corresponding to this narrative text description might be "S62.630A", which corresponds to the standardized text string "initial encounter for closed displaced fracture of distal phalanx of right index finger". However, the ICH-10-CM diagnostic encoding refers to this portion of the narrative text description, and there may be additional narrative text which is not relevant to this particular diagnostic encoding. To create training data, an annotation must be created that links a specific encoding to this specific portion of the narrative text.

An embodiment selects an encoding, formed according to a standardized encoding scheme that includes a standardized text string representation, from the metadata corresponding to the narrative text. The embodiment selects a specified portion of the standardized text string for use as an anchor term. In one embodiment, the specified portion is one word of the standardized text string. In one embodiment, the specified portion is the first word of the standardized text string. In another embodiment, the specified portion is a random word of the standardized text string, selected using a pseudo-random number generation function of a software implementation. Other anchor term selection schemes are also possible and contemplated within the scope of the illustrative embodiments.

Continuing the MedDRA example discussed herein, suppose the embodiment has selected the MedDRA Preferred Term "stomach pain". The embodiment selects as anchor term the first word of the MedDRA Preferred Term, "stomach".

An embodiment searches the narrative text for the selected anchor term. If the embodiment fails to locate the selected anchor term in the narrative text, the embodiment selects a different anchor term from a specified portion of the standardized text string, and repeats the search of the narrative text for the new anchor term. If, after a predetermined number of attempts, the embodiment fails to locate the selected anchor term in the narrative text, the embodiment flags the narrative text and corresponding metadata as having an error, and possibly requiring human intervention.

If the embodiment locates the selected anchor term in the narrative text, the embodiment constructs a text window. The text window includes the anchor term and a portion of narrative text within a predetermined distance from the anchor term. In one embodiment, the predetermined distance is measured using a number of words. In one embodiment, the initial text window includes the anchor term and one word next to the anchor term. In another embodiment, the initial text window includes the anchor term and the one word immediately before and after the anchor term, if not separated by punctuation. In another embodiment, the initial text window includes the anchor term and the two words immediately before and after the anchor term, if not separated by punctuation. Other sizes and schemes for determining an initial text window are also possible and contemplated within the scope of the illustrative embodiments.

An embodiment proposes a new encoding, formed according to the same standardized encoding scheme as the initial encoding, corresponding to the text in the text window. To formulate the proposal, an embodiment uses a Natural Language Processing (NLP) engine. In one embodiment, a machine learning classifier (for example, a convolutional neural network) is used to propose the new encoding. Such a machine learning classifier is trained before use with training data including pairs of text strings and corresponding encodings.

Continuing the MedDRA example discussed herein, from the anchor term "stomach", the embodiment constructs a text window including the anchor term and the two words immediately before the anchor term—here, "trouble in stomach after taking". The embodiment proposes a new encoding corresponding to "trouble in stomach after taking"—here, the MedDRA Preferred Term "stomach pain".

An embodiment compares the proposed new encoding with the original encoding. If the two encodings are identical, the embodiment annotates the text of the text window with the encoding. The annotation creates new data linking the text of the text window with the encoding.

Continuing the MedDRA example discussed herein, because the proposed new encoding (the MedDRA Preferred Term "stomach pain") is the same as the original encoding, the embodiment annotates the text "trouble in stomach after taking" with the MedDRA Preferred Term "stomach pain".

If the two encodings are not identical, the embodiment constructs a new text window including the anchor term and a portion of narrative text within a different predetermined distance from the anchor term. One embodiment expands the text window by a predetermined amount. An embodiment proposes a new encoding, formed according to the same standardized encoding scheme as the initial encoding, corresponding to the text in the new text window, and compares the new encoding with the original encoding. If the two encodings are identical, the embodiment annotates the text of the new text window with the encoding. If the two encodings are not identical, an embodiment once again performs the new text window construction and encoding proposal until the embodiment proposes an encoding identical to the original encoding, or the embodiment determines that a proposed encoding cannot be found.

One embodiment determines that a proposed encoding cannot be found when the embodiment reaches a predetermined limit of iterations on text window construction. Another embodiment determines that a proposed encoding cannot be found when the embodiment reaches a predetermined text window size or a predetermined distance from the anchor term. Other criteria for determining that a proposed encoding cannot be found are also possible and contemplated within the scope of the illustrative embodiments. If an embodiment determines that a proposed encoding cannot be found, the embodiment flags the narrative text and corresponding metadata as having an error, and possibly requiring human intervention.

The manner of encoding-assisted annotation of narrative text described herein is unavailable in the presently available methods in the technological field of endeavor pertaining to training data generation for NLP implementations. A method of an embodiment described herein, when implemented to execute on a device or data processing system, comprises substantial advancement of the functionality of that device or data processing system in using existing metadata including encodings according to an standardized encoding scheme to annotate narrative text.

The illustrative embodiments are described with respect to certain types of encodings, encoding schemes, metadata, anchor terms, text windows, distances, sizes, thresholds, devices, data processing systems, environments, components, and applications only as examples. Any specific manifestations of these and other similar artifacts are not intended to be limiting to the invention. Any suitable manifestation of these and other similar artifacts can be selected within the scope of the illustrative embodiments.

Furthermore, the illustrative embodiments may be implemented with respect to any type of data, data source, or access to a data source over a data network. Any type of data storage device may provide the data to an embodiment of the invention, either locally at a data processing system or over a data network, within the scope of the invention. Where an embodiment is described using a mobile device, any type of data storage device suitable for use with the mobile device may provide the data to such embodiment, either locally at the mobile device or over a data network, within the scope of the illustrative embodiments.

The illustrative embodiments are described using specific code, designs, architectures, protocols, layouts, schematics, and tools only as examples and are not limiting to the illustrative embodiments. Furthermore, the illustrative embodiments are described in some instances using particular software, tools, and data processing environments only as an example for the clarity of the description. The illustrative embodiments may be used in conjunction with other comparable or similarly purposed structures, systems, applications, or architectures. For example, other comparable mobile devices, structures, systems, applications, or architectures therefor, may be used in conjunction with such embodiment of the invention within the scope of the invention. An illustrative embodiment may be implemented in hardware, software, or a combination thereof.

The examples in this disclosure are used only for the clarity of the description and are not limiting to the illustrative embodiments. Additional data, operations, actions, tasks, activities, and manipulations will be conceivable from this disclosure and the same are contemplated within the scope of the illustrative embodiments.

Any advantages listed herein are only examples and are not intended to be limiting to the illustrative embodiments. Additional or different advantages may be realized by specific illustrative embodiments. Furthermore, a particular illustrative embodiment may have some, all, or none of the advantages listed above.

Figure 1:
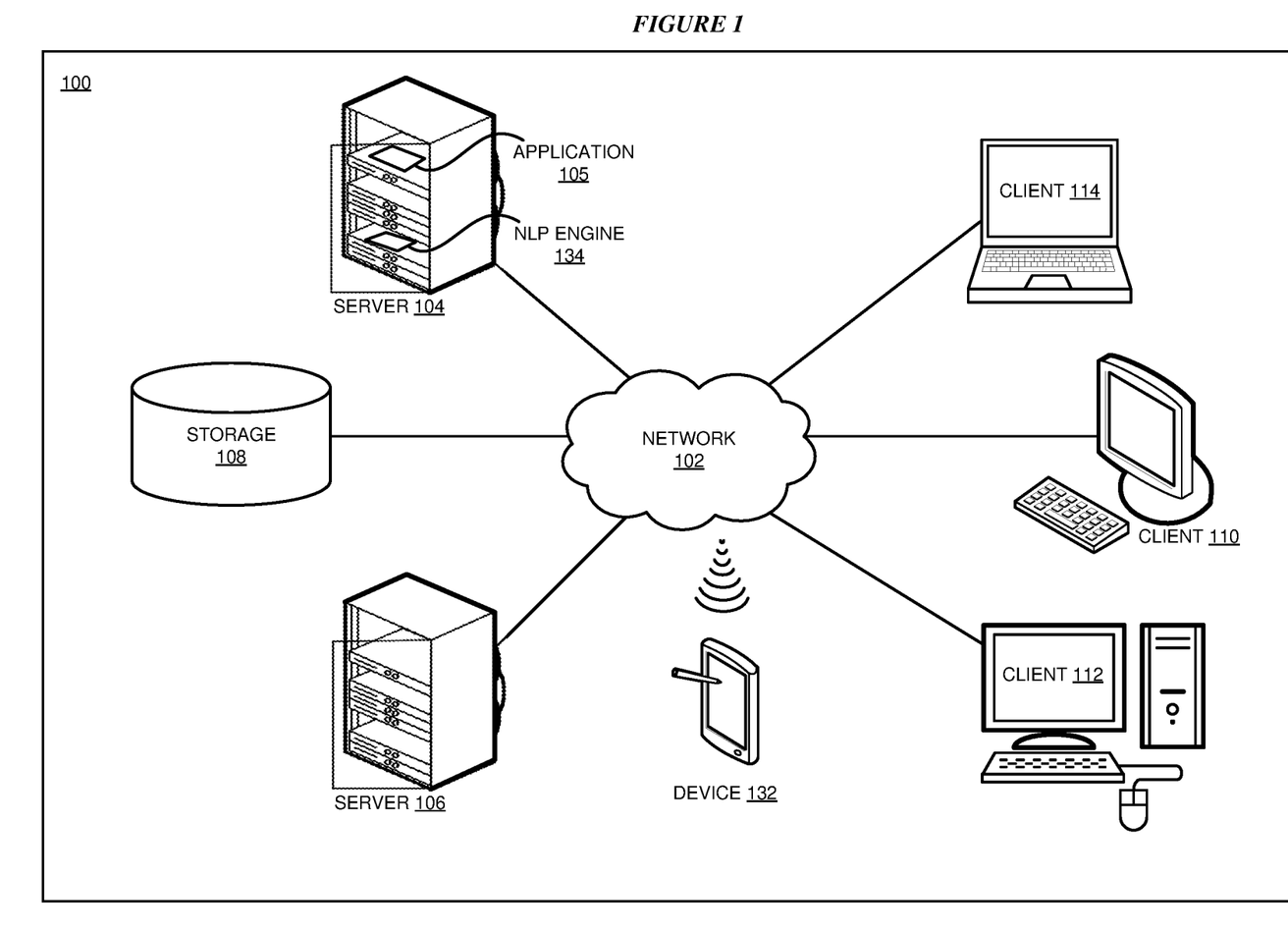
FIG. 1 depicts a block diagram of a network of data processing systems in which illustrative embodiments may be implemented.
Figure 2:
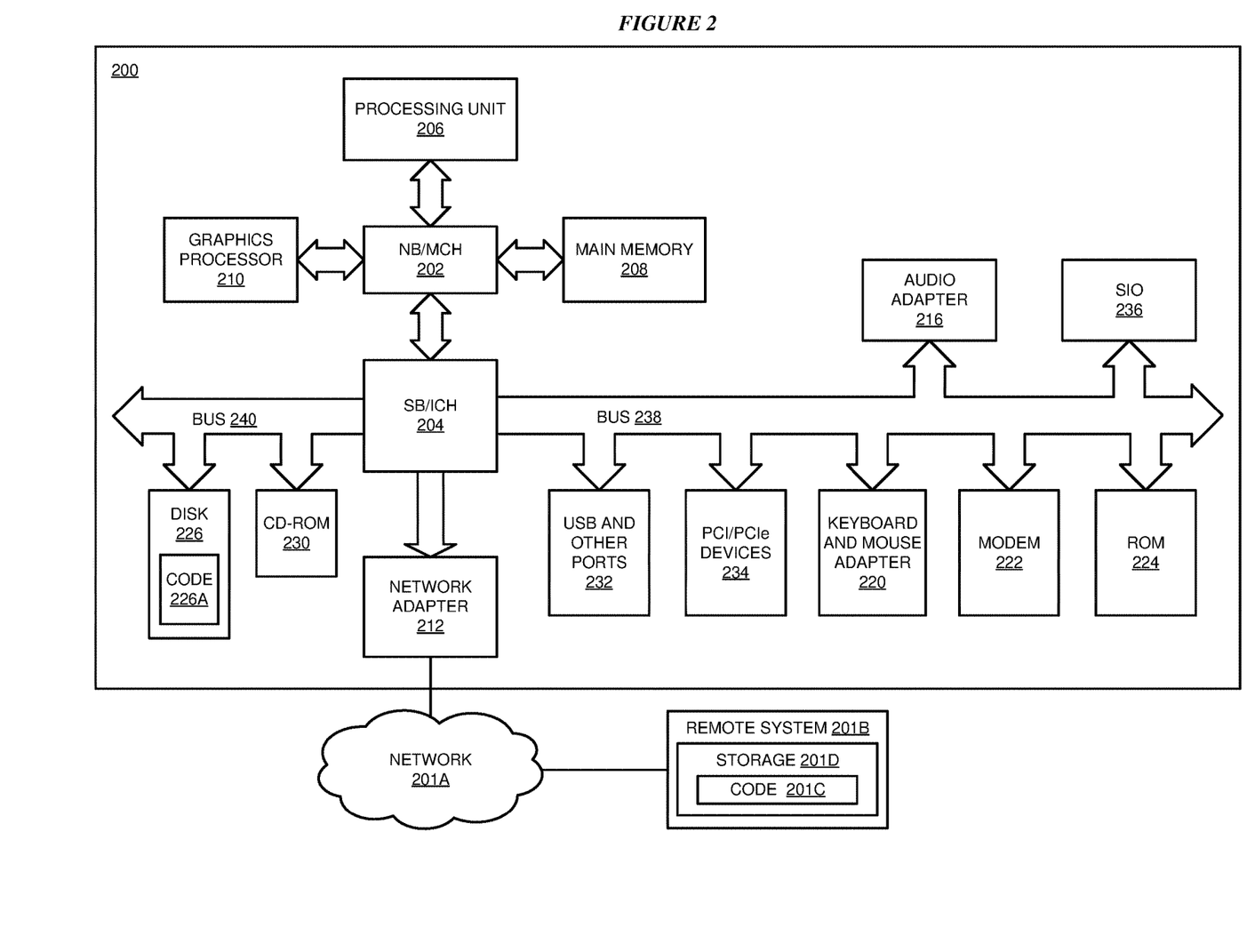
FIG. 2 depicts a block diagram of a data processing system in which illustrative embodiments may be implemented.

With reference to the figures and in particular with reference to FIGS. 1 and 2, these figures are example diagrams of data processing environments in which illustrative embodiments may be implemented. FIGS. 1 and 2 are only examples and are not intended to assert or imply any limitation with regard to the environments in which different embodiments may be implemented. A particular implementation may make many modifications to the depicted environments based on the following description.

FIG. 1 depicts a block diagram of a network of data processing systems in which illustrative embodiments may be implemented. Data processing environment 100 is a network of computers in which the illustrative embodiments may be implemented. Data processing environment 100 includes network 102. Network 102 is the medium used to provide communications links between various devices and computers connected together within data processing environment 100. Network 102 may include connections, such as wire, wireless communication links, or fiber optic cables.

Clients or servers are only example roles of certain data processing systems connected to network 102 and are not intended to exclude other configurations or roles for these data processing systems. Server 104 and server 106 couple to network 102 along with storage unit 108. Software applications may execute on any computer in data processing environment 100. Clients 110, 112, and 114 are also coupled to network 102. A data processing system, such as server 104 or 106, or client 110, 112, or 114 may contain data and may have software applications or software tools executing thereon.

Only as an example, and without implying any limitation to such architecture, FIG. 1 depicts certain components that are usable in an example implementation of an embodiment. For example, servers 104 and 106, and clients 110, 112, 114, are depicted as servers and clients only as example and not to imply a limitation to a client-server architecture. As another example, an embodiment can be distributed across several data processing systems and a data network as shown, whereas another embodiment can be implemented on a single data processing system within the scope of the illustrative embodiments. Data processing systems 104, 106, 110, 112, and 114 also represent example nodes in a cluster, partitions, and other configurations suitable for implementing an embodiment.

Device 132 is an example of a device described herein. For example, device 132 can take the form of a smartphone, a tablet computer, a laptop computer, client 110 in a stationary or a portable form, a wearable computing device, or any other suitable device. Any software application described as executing in another data processing system in FIG. 1 can be configured to execute in device 132 in a similar manner. Any data or information stored or produced in another data processing system in FIG. 1 can be configured to be stored or produced in device 132 in a similar manner.

Application 105 implements an embodiment described herein. Application 105 also makes use of NLP engine 134. Application 105 and NLP engine 134 may execute in any of servers 104 and 106, clients 110, 112, and 114, and device 132.

Servers 104 and 106, storage unit 108, and clients 110, 112, and 114, and device 132 may couple to network 102 using wired connections, wireless communication protocols, or other suitable data connectivity. Clients 110, 112, and 114 may be, for example, personal computers or network computers.

In the depicted example, server 104 may provide data, such as boot files, operating system images, and applications to clients 110, 112, and 114. Clients 110, 112, and 114 may be clients to server 104 in this example. Clients 110, 112, 114, or some combination thereof, may include their own data, boot files, operating system images, and applications. Data processing environment 100 may include additional servers, clients, and other devices that are not shown.

In the depicted example, data processing environment 100 may be the Internet. Network 102 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client-server environment in which the illustrative embodiments may be implemented. A client-server environment enables software applications and data to be distributed across a network such that an application functions by using the interactivity between a client data processing system and a server data processing system. Data processing environment 100 may also employ a service oriented architecture where interoperable software components distributed across a network may be packaged together as coherent business applications. Data processing environment 100 may also take the form of a cloud, and employ a cloud computing model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

With reference to FIG. 2, this figure depicts a block diagram of a data processing system in which illustrative embodiments may be implemented. Data processing system 200 is an example of a computer, such as servers 104 and 106, or clients 110, 112, and 114 in FIG. 1, or another type of device in which computer usable program code or instructions implementing the processes may be located for the illustrative embodiments.

Data processing system 200 is also representative of a data processing system or a configuration therein, such as data processing system 132 in FIG. 1 in which computer usable program code or instructions implementing the processes of the illustrative embodiments may be located. Data processing system 200 is described as a computer only as an example, without being limited thereto. Implementations in the form of other devices, such as device 132 in FIG. 1, may modify data processing system 200, such as by adding a touch interface, and even eliminate certain depicted components from data processing system 200 without departing from the general description of the operations and functions of data processing system 200 described herein.

In the depicted example, data processing system 200 employs a hub architecture including North Bridge and memory controller hub (NB/MCH) 202 and South Bridge and input/output (I/O) controller hub (SB/ICH) 204. Processing unit 206, main memory 208, and graphics processor 210 are coupled to North Bridge and memory controller hub (NB/MCH) 202. Processing unit 206 may contain one or more processors and may be implemented using one or more heterogeneous processor systems. Processing unit 206 may be a multi-core processor. Graphics processor 210 may be coupled to NB/MCH 202 through an accelerated graphics port (AGP) in certain implementations.

In the depicted example, local area network (LAN) adapter 212 is coupled to South Bridge and I/O controller hub (SB/ICH) 204. Audio adapter 216, keyboard and mouse adapter 220, modem 222, read only memory (ROM) 224, universal serial bus (USB) and other ports 232, and PCI/PCIe devices 234 are coupled to South Bridge and I/O controller hub 204 through bus 238. Hard disk drive (HDD) or solid-state drive (SSD) 226 and CD-ROM 230 are coupled to South Bridge and I/O controller hub 204 through bus 240. PCI/PCIe devices 234 may include, for example, Ethernet adapters, add-in cards, and PC cards for notebook computers. PCI uses a card bus controller, while PCIe does not. ROM 224 may be, for example, a flash binary input/output system (BIOS). Hard disk drive 226 and CD-ROM 230 may use, for example, an integrated drive electronics (IDE), serial advanced technology attachment (SATA) interface, or variants such as external-SATA (eSATA) and micro-SATA (mSATA). A super I/O (SIO) device 236 may be coupled to South Bridge and I/O controller hub (SB/ICH) 204 through bus 238.

Memories, such as main memory 208, ROM 224, or flash memory (not shown), are some examples of computer usable storage devices. Hard disk drive or solid state drive 226, CD-ROM 230, and other similarly usable devices are some examples of computer usable storage devices including a computer usable storage medium.

An operating system runs on processing unit 206. The operating system coordinates and provides control of various components within data processing system 200 in FIG. 2. The operating system may be a commercially available operating system for any type of computing platform, including but not limited to server systems, personal computers, and mobile devices. An object oriented or other type of programming system may operate in conjunction with the operating system and provide calls to the operating system from programs or applications executing on data processing system 200.

Instructions for the operating system, the object-oriented programming system, and applications or programs, such as application 105 and NLP engine 134 in FIG. 1, are located on storage devices, such as in the form of code 226A on hard disk drive 226, and may be loaded into at least one of one or more memories, such as main memory 208, for execution by processing unit 206. The processes of the illustrative embodiments may be performed by processing unit 206 using computer implemented instructions, which may be located in a memory, such as, for example, main memory 208, read only memory 224, or in one or more peripheral devices.

Furthermore, in one case, code 226A may be downloaded over network 201A from remote system 201B, where similar code 201C is stored on a storage device 201D. in another case, code 226A may be downloaded over network 201A to remote system 201B, where downloaded code 201C is stored on a storage device 201D.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. In addition, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may comprise one or more buses, such as a system bus, an I/O bus, and a PCI bus. Of course, the bus system may be implemented using any type of communications fabric or architecture that provides for a transfer of data between different components or devices attached to the fabric or architecture.

A communications unit may include one or more devices used to transmit and receive data, such as a modem or a network adapter. A memory may be, for example, main memory 208 or a cache, such as the cache found in North Bridge and memory controller hub 202. A processing unit may include one or more processors or CPUs.

The depicted examples in FIGS. 1-2 and above-described examples are not meant to imply architectural limitations. For example, data processing system 200 also may be a tablet computer, laptop computer, or telephone device in addition to taking the form of a mobile or wearable device.

Where a computer or data processing system is described as a virtual machine, a virtual device, or a virtual component, the virtual machine, virtual device, or the virtual component operates in the manner of data processing system 200 using virtualized manifestation of some or all components depicted in data processing system 200. For example, in a virtual machine, virtual device, or virtual component, processing unit 206 is manifested as a virtualized instance of all or some number of hardware processing units 206 available in a host data processing system, main memory 208 is manifested as a virtualized instance of all or some portion of main memory 208 that may be available in the host data processing system, and disk 226 is manifested as a virtualized instance of all or some portion of disk 226 that may be available in the host data processing system. The host data processing system in such cases is represented by data processing system 200.

Figure 3:
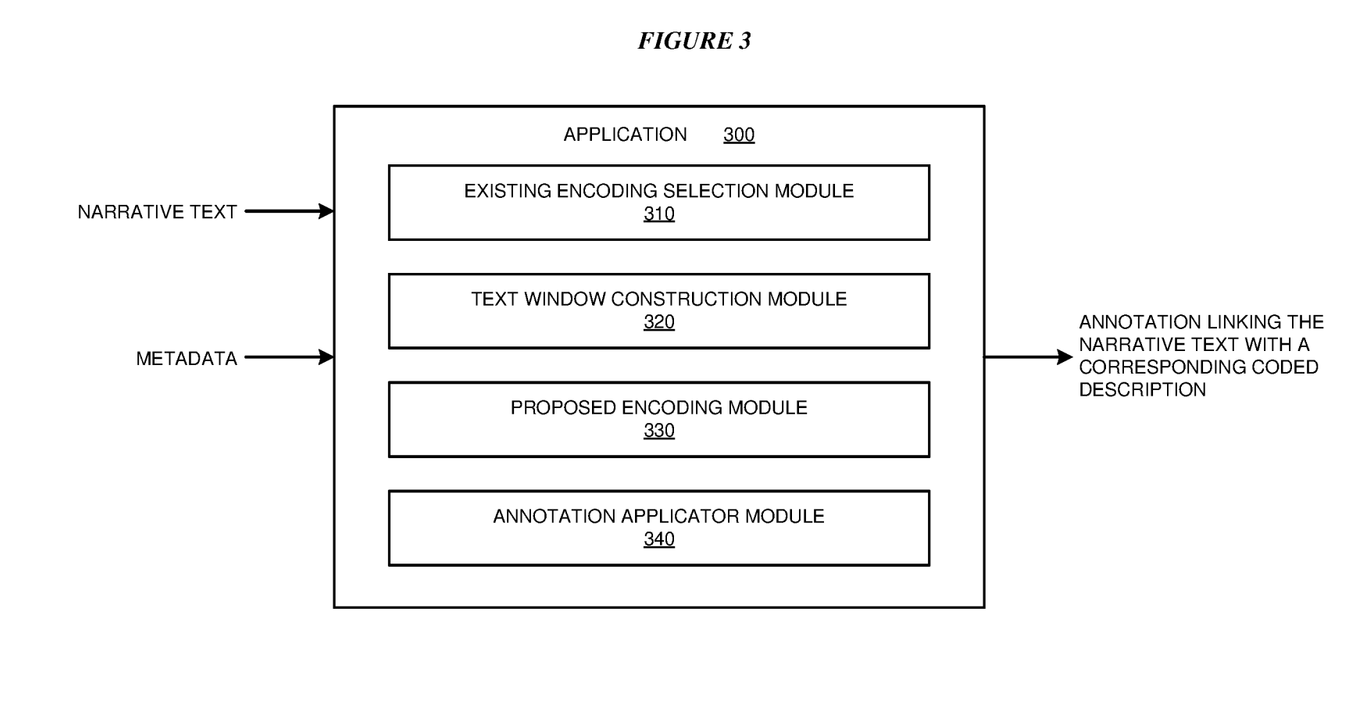
FIG. 3 depicts a block diagram of an example configuration for encoding-assisted annotation of narrative text in accordance with an illustrative embodiment.

With reference to FIG. 3, this figure depicts a block diagram of an example configuration for encoding-assisted annotation of narrative text in accordance with an illustrative embodiment. Application 300 is an example of application 105 in FIG. 1 and executes any of servers 104 and 106, clients 110, 112, and 114, and device 132 in FIG. 1.

Application 300 receives, for annotation, a narrative text description and metadata corresponding to the narrative text description. The metadata includes at least one encoding, formed according to a standardized encoding scheme, corresponding to the narrative text. Existing encoding selection module 310 selects an encoding, formed according to a standardized encoding scheme that includes a standardized text string representation, from the metadata corresponding to the narrative text.

Text window construction module 320 selects a specified portion of the standardized text string for use as an anchor term. Module 320 also searches the narrative text for the selected anchor term. If module 320 locates the selected anchor term in the narrative text, module 320 constructs a text window. The text window includes the anchor term and a portion of narrative text within a predetermined distance from the anchor term.

Proposed encoding module 330 proposes a new encoding, formed according to the same standardized encoding scheme as the initial encoding, corresponding to the text in the text window. Module 330 compares the proposed new encoding with the original encoding. If the two encodings are identical, annotation applicator module 340 annotates the text of the text window with the encoding. The annotation creates new data linking the text of the text window with the encoding.

Figure 4:
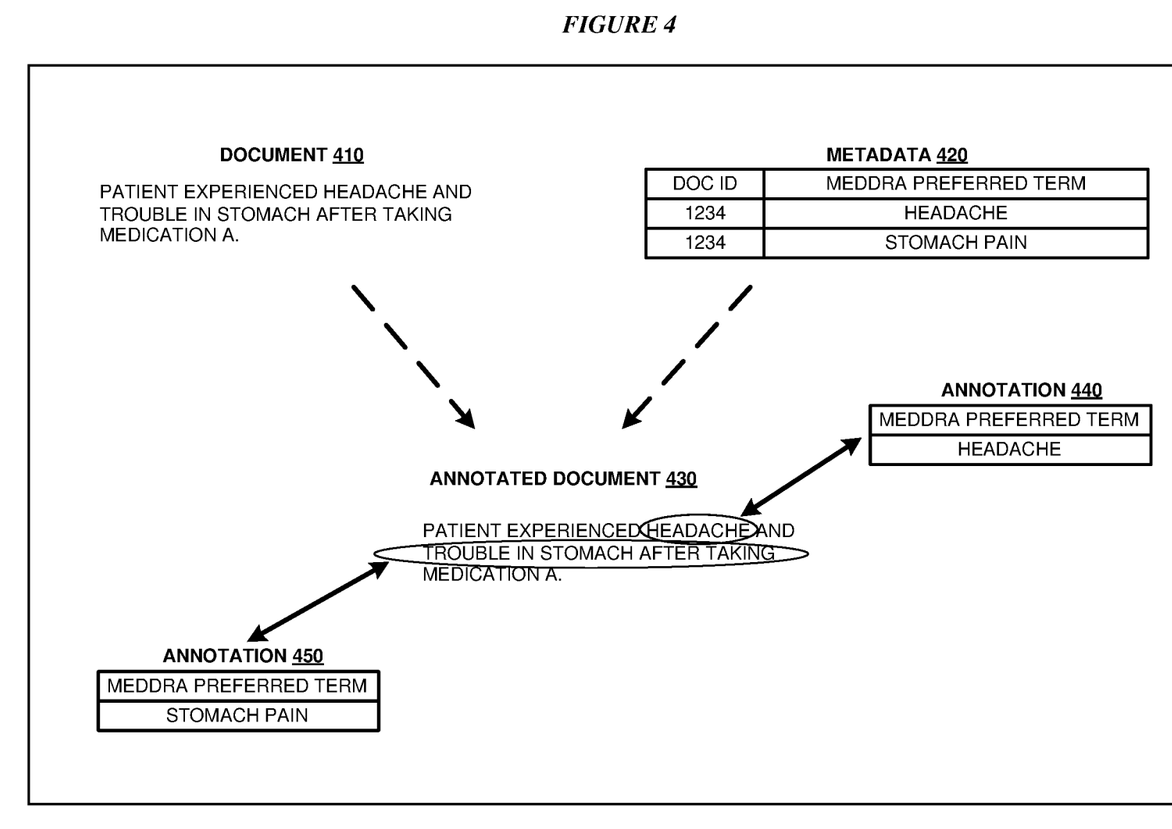
FIG. 4 depicts an example of encoding-assisted annotation of narrative text in accordance with an illustrative embodiment.

With reference to FIG. 4, this figure depicts an example of encoding-assisted annotation of narrative text in accordance with an illustrative embodiment. FIG. 4 depicts the results of application 300 in FIG. 3.

Here, application 300 receives, for annotation, a narrative text description and metadata corresponding to the narrative text description. The metadata includes at least one encoding, formed according to a standardized encoding scheme, corresponding to the narrative text. Document 410 is an example of a narrative text description, and metadata 420 is an example of metadata corresponding to the narrative text description in document 410. In particular, document 410 is an example of an adverse event related to a medication, and metadata 420 is an example of metadata corresponding to the narrative text description including two encodings according to the MedDRA standardized encoding scheme—here, "headache" and "stomach pain". Annotated document 430 shows the results of execution of application 300. Here, annotation 440 links "headache" in the narrative text with the MedDRA encoding of "headache". Annotation 450 links "trouble in stomach after taking" in the narrative text with the MedDRA encoding of "stomach pain".

Figure 5:
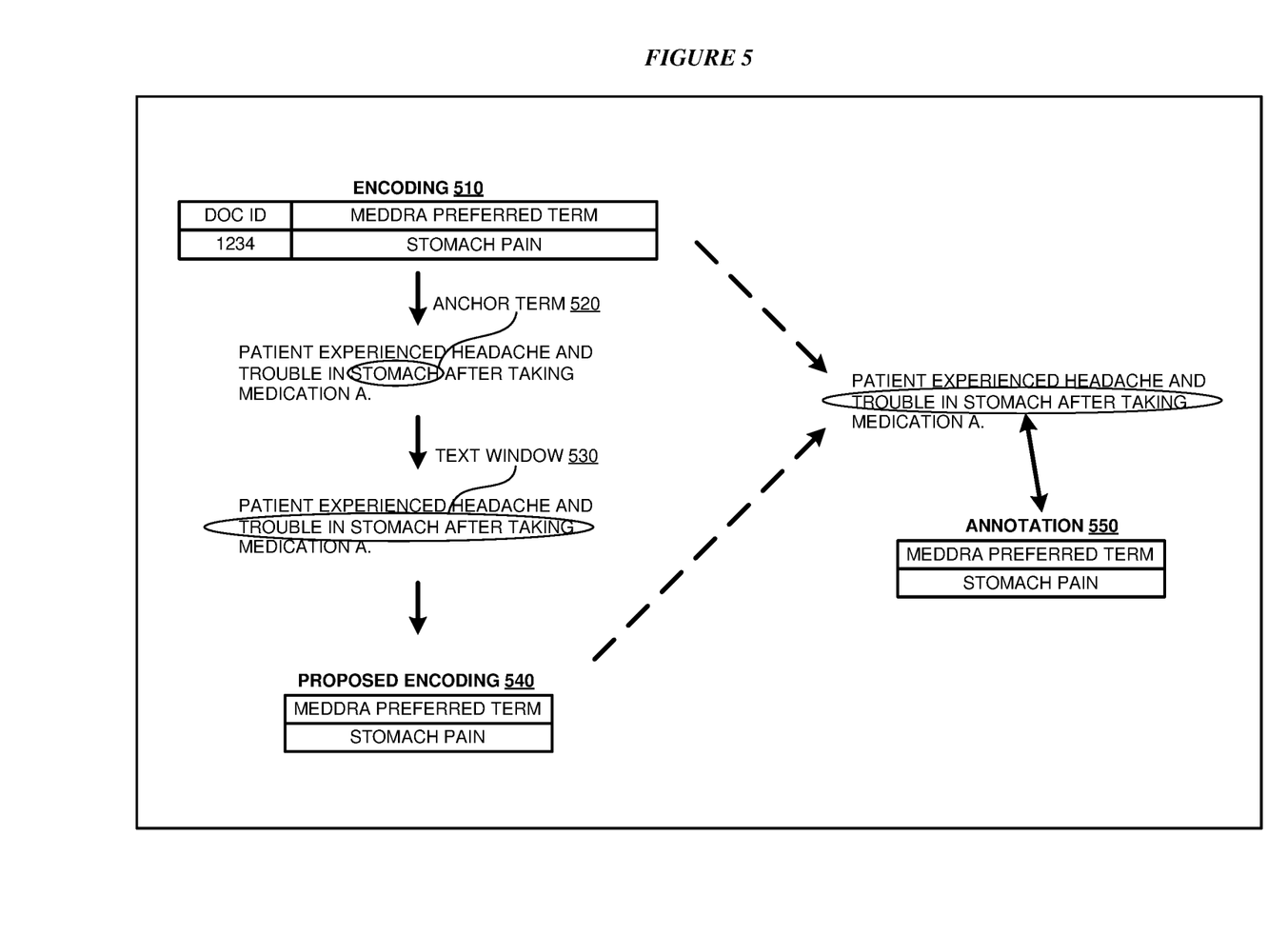
FIG. 5 depicts another example of encoding-assisted annotation of narrative text in accordance with an illustrative embodiment.

With reference to FIG. 5, this figure depicts another example of encoding-assisted annotation of narrative text in accordance with an illustrative embodiment. FIG. 5 depicts more detail of the creation of annotation 450 in FIG. 4 using application 300 in FIG. 3.

Suppose application 300 has selected encoding 510, the MedDRA Preferred Term "stomach pain". Application 300 selects as anchor term 520 the first word of the MedDRA Preferred Term, "stomach", and locates "stomach" within the narrative text. Application 300 constructs text window 530 including the anchor term and a portion of narrative text within a predetermined distance from the anchor term—here, "trouble in stomach after taking". Application 300 proposes a new encoding corresponding to "trouble in stomach after taking"—here, proposed encoding 540, the MedDRA Preferred Term "stomach pain". Since the two encodings are identical, application 300 creates annotation 550 linking "trouble in stomach after taking" with the MedDRA Preferred Term "stomach pain".

Figure 6:
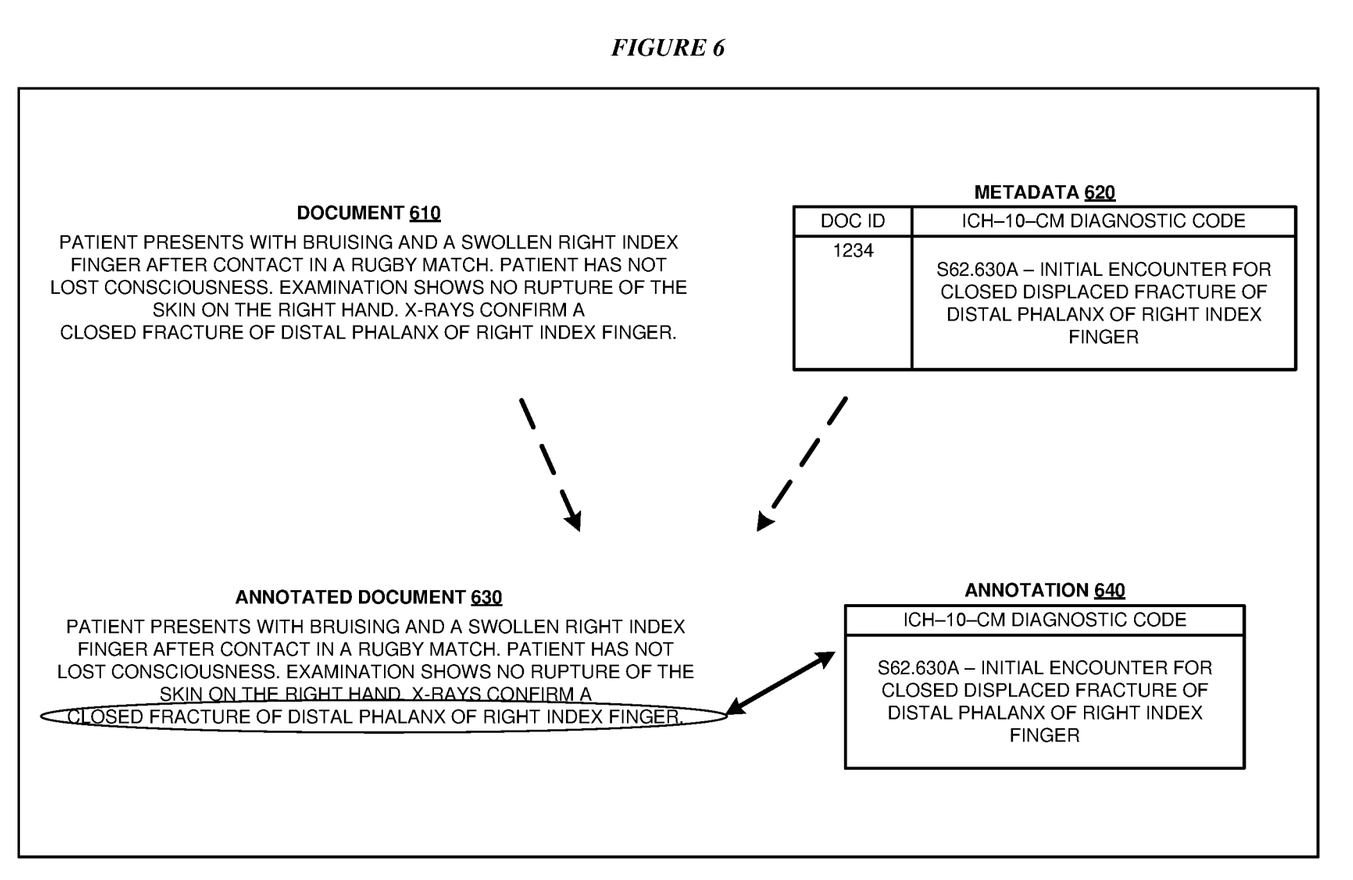
FIG. 6 depicts another example of encoding-assisted annotation of narrative text in accordance with an illustrative embodiment.

With reference to FIG. 6, this figure depicts another example of encoding-assisted annotation of narrative text in accordance with an illustrative embodiment. FIG. 6 depicts the results of application 300 in FIG. 3.

Here, application 300 receives, for annotation, a narrative text description and metadata corresponding to the narrative text description. The metadata includes at least one encoding, formed according to a standardized encoding scheme, corresponding to the narrative text. Document 610 is an example of a narrative text description, and metadata 620 is an example of metadata corresponding to the narrative text description in document 610. In particular, document 610 is an example of a report of a patient encounter, and metadata 620 is an example of metadata corresponding to the narrative text description including an encoding according to the ICH-10-CM encoding scheme—here, "S62.630A—initial encounter for closed displaced fracture of distal phalanx of right index finger". Annotated document 630 shows the results of execution of application 300. Here, annotation 640 links "closed fracture of distal phalanx of right index finger"" in the narrative text with the ICH-10-CM encoding of "S62.630A—initial encounter for closed displaced fracture of distal phalanx of right index finger".

Figure 7:
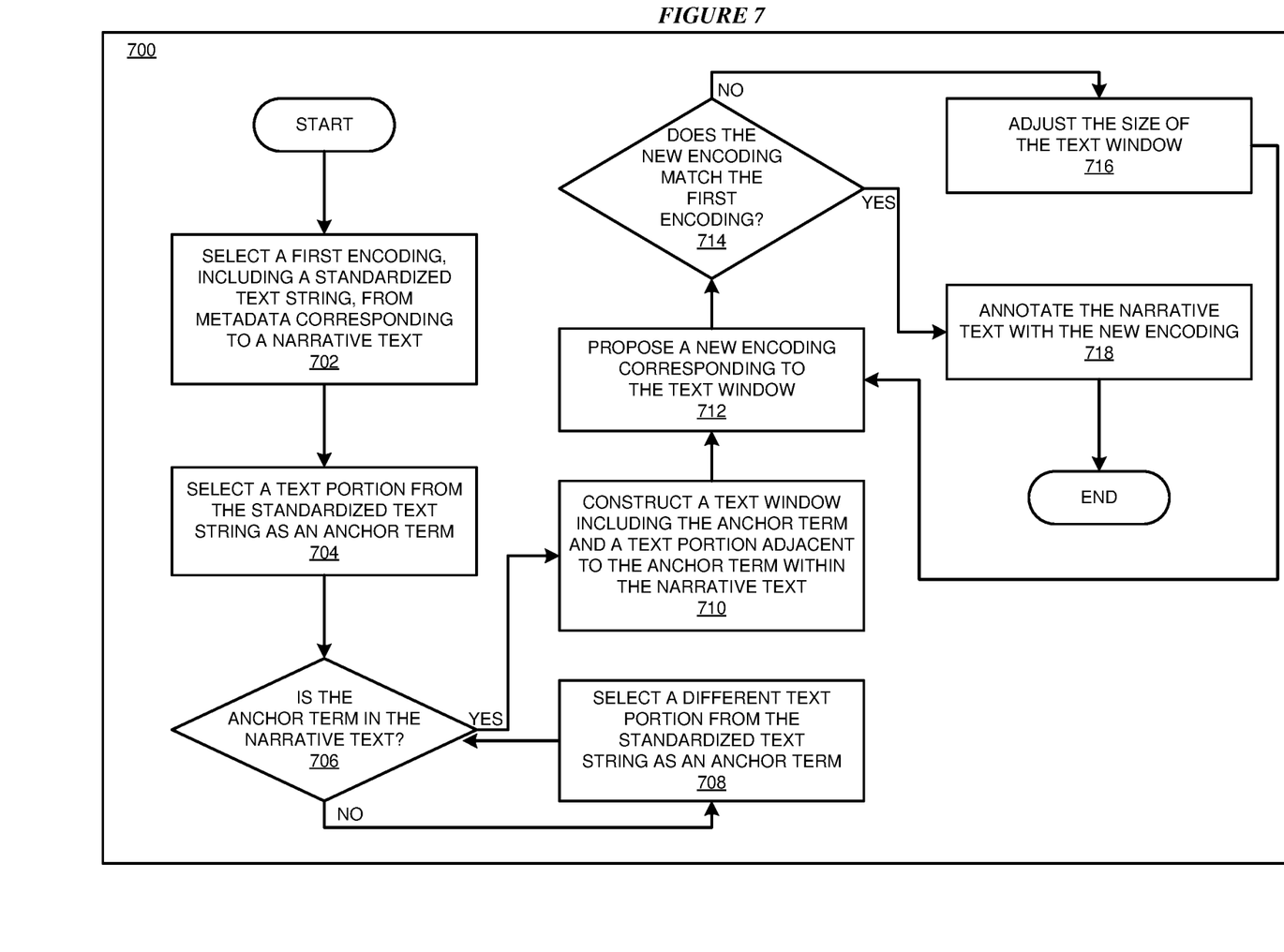
FIG. 7 depicts a flowchart of an example process for encoding-assisted annotation of narrative text in accordance with an illustrative embodiment.

With reference to FIG. 7, this figure depicts a flowchart of an example process for encoding-assisted annotation of narrative text in accordance with an illustrative embodiment. Process 700 can be implemented in application 300 in FIG. 3.

In block 702, the application selects a first encoding, including a standardized text string, from metadata corresponding to a narrative text. In block 704, the application selects a specified portion of the standardized text string from the standardized text string for use as an anchor term. In block 706, the application attempts to locate the anchor term in the narrative text. If the application fails to locate the anchor term in the narrative text ("NO" path of block 706, in block 708 the application selects a different specified portion of the standardized text string from the standardized text string for use as an anchor term, then returns to block 706. If the application locates the anchor term in the narrative text ("YES" path of block 706, in block 710 the application constructs a text window. The text window includes the anchor term and a portion of narrative text within a predetermined distance from the anchor term. In block 712, the application proposes a new encoding, formed according to the same standardized encoding scheme as the initial encoding, corresponding to the text in the text window. In block 714, the application compares the proposed new encoding with the original encoding. If the two encodings are identical ("YES" path of block 714), in block 718 the application annotates the text of the text window with the encoding, then ends. Otherwise ("NO" path of block 714), in block 716 the application adjusts the size of the text window, then returns to block 712.

Thus, a computer implemented method, system or apparatus, and computer program product are provided in the illustrative embodiments for encoding-assisted annotation of narrative text and other related features, functions, or operations. Where an embodiment or a portion thereof is described with respect to a type of device, the computer implemented method, system or apparatus, the computer program product, or a portion thereof, are adapted or configured for use with a suitable and comparable manifestation of that type of device.

Where an embodiment is described as implemented in an application, the delivery of the application in a Software as a Service (SaaS) model is contemplated within the scope of the illustrative embodiments. In a SaaS model, the capability of the application implementing an embodiment is provided to a user by executing the application in a cloud infrastructure. The user can access the application using a variety of client devices through a thin client interface such as a web browser (e.g., web-based e-mail), or other light-weight client-applications. The user does not manage or control the underlying cloud infrastructure including the network, servers, operating systems, or the storage of the cloud infrastructure. In some cases, the user may not even manage or control the capabilities of the SaaS application. In some other cases, the SaaS implementation of the application may permit a possible exception of limited user-specific application configuration settings.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method comprising:
selecting, from within metadata describing a narrative text, a first encoding, the first encoding comprising a standardized text string, the first encoding formed according to an encoding scheme;
marking, as an anchor term, a portion within the standardized text string of the first encoding, wherein the portion comprises a word selected randomly from the standardized text string using a pseudo-random number generator;
finding the anchor term within the narrative text;
defining a text window within the narrative text responsive to finding the anchor term within the narrative text, the text window comprising an instance of the anchor term within the narrative text and all words of the narrative text within a predetermined distance before and after the instance;
encoding, according to the encoding scheme using a trained machine learning classifier, the text window into a second encoding, the trained machine learning classifier trained before use with training data comprising pairs of text strings and corresponding encodings;
determining that a mismatch exists between the second encoding and the first encoding;
defining an expanded text window within the narrative text responsive to the mismatch between the second encoding and the first encoding, the expanded text window comprising an expansion of the text window by a predetermined amount;
encoding, according to the encoding scheme using the trained machine learning classifier, the expanded text window into a third encoding; and
annotating, responsive to the third encoding being identical to the first encoding, the narrative text, the annotating creating new data linking text of the narrative text within the expanded text window with the third encoding.

2. The method of claim 1, wherein the narrative text describes an adverse event and the encoding scheme encodes the adverse event as a standardized hierarchy of text descriptions.

3. The method of claim 1, wherein the narrative text describes a medical report of a patient and the encoding scheme encodes a diagnosis relating to the medical report.

4. The method of claim 1, wherein the portion comprises a word of the standardized text string of the first encoding.

5. The method of claim 4, wherein the word comprises a first word of the standardized text string of the first encoding.

6. A computer usable program product comprising one or more computer-readable storage media, and program instructions stored on at least one of the one or more storage media, the stored program instructions comprising:
program instructions to select, from within metadata describing a narrative text, a first encoding, the first encoding comprising a standardized text string, the first encoding formed according to an encoding scheme;
program instructions to mark, as an anchor term, a portion within the standardized text string of the first encoding, wherein the portion comprises a word selected randomly from the standardized text string using a pseudo-random number generator;
program instructions to find the anchor term within the narrative text;
program instructions to define a text window within the narrative text responsive to finding the anchor term within the narrative text, the text window comprising an instance of the anchor term within the narrative text and all words of the narrative text within a predetermined distance before and after the instance;
program instructions to encode, according to the encoding scheme using a trained machine learning classifier, the text window into a second encoding, the trained machine learning classifier trained before use with training data comprising pairs of text strings and corresponding encodings;
program instructions to determine that a mismatch exists between the second encoding and the first encoding;
program instructions to define an expanded text window within the narrative text responsive to the mismatch between the second encoding and the first encoding, the expanded text window comprising an expansion of the text window by a predetermined amount;

program instructions to encode, according to the encoding scheme using the trained machine learning classifier, the expanded text window into a third encoding; and program instructions to annotate, responsive to the third encoding being identical to the first encoding, the narrative text, the annotating creating new data linking text of the narrative text within the expanded text window with the third encoding.

7. The computer usable program product of claim 6, wherein the narrative text describes an adverse event and the encoding scheme encodes the adverse event as a standardized hierarchy of text descriptions.

8. The computer usable program product of claim 6, wherein the narrative text describes a medical report of a patient and the encoding scheme encodes a diagnosis relating to the medical report.

9. The computer usable program product of claim 6, wherein the portion comprises a word of the standardized text string of the first encoding.

10. The computer usable program product of claim 9, wherein the word comprises a first word of the standardized text string of the first encoding.

11. The computer usable program product of claim 6, wherein the stored program instructions are stored in a computer readable storage medium in a data processing system, and wherein the stored program instructions are transferred over a network from a remote data processing system.

12. The computer usable program product of claim 6, wherein the stored program instructions are stored in a computer readable storage medium in a server data processing system, and wherein the stored program instructions are downloaded over a network to a remote data processing system for use in a computer readable storage medium associated with the remote data processing system.

13. A computer system comprising one or more processors, one or more computer-readable memories, and one or more computer-readable storage media, and program instructions stored on at least one of the one or more storage media for execution by at least one of the one or more processors via at least one of the one or more memories, the stored program instructions comprising:

program instructions to select, from within metadata describing narrative text, a first encoding, the first encoding comprising a standardized text string, the first encoding formed according to an encoding scheme;

program instructions to mark, as an anchor term, a portion within the standardized text string of the first encoding, wherein the portion comprises a word selected randomly from the standardized text string using a pseudo-random number generator;

program instructions to find the anchor term within the narrative text;

program instructions to define a text window within the narrative text responsive to finding the anchor term within the narrative text, the text window comprising an instance of the anchor term within the narrative text and all words of the narrative text within a predetermined distance before and after the instance;

program instructions to encode, according to the encoding scheme using a trained machine learning classifier, the text window into a second encoding, the trained machine learning classifier trained before use with training data comprising pairs of text strings and corresponding encodings;

program instructions to determine that a mismatch exists between the second encoding and the first encoding;

program instructions to define an expanded text window within the narrative text responsive to the mismatch between the second encoding and the first encoding, the expanded text window comprising an expansion of the text window by a predetermined amount;

program instructions to encode, according to the encoding scheme using the trained machine learning classifier, the expanded text window into a third encoding; and program instructions to annotate, responsive to the third encoding being identical to the first encoding, the narrative text, the annotating creating new data linking text of the narrative text within the expanded text window with the third encoding.

14. The computer system of claim 13, wherein the narrative text describes an adverse event and the encoding scheme encodes the adverse event as a standardized hierarchy of text descriptions.

* * * * *